(12) United States Patent
Bhardwaj et al.

(10) Patent No.: US 9,301,957 B2
(45) Date of Patent: Apr. 5, 2016

(54) IMMEDIATE RELEASE 4-METHYL-3-4[[4-(3-PYRIDINYL)-2-PYRIMIDINYL] AMINO]-N-[5-(4-METHYL-1H-IMIDAZOL-1-YL)-3-(TRIFLUOROMETHYL)PHENYL] BENZAMIDE FORMULATION

(71) Applicants: Upkar Bhardwaj, Coram, NY (US); Ann Reese Comfort, New York, NY (US); Ping Li, Basking Ridge, NJ (US); Shoufeng Li, Basking Ridge, NJ (US); Alexey Makarov, Montclair, NJ (US); Mangesh Sadashiv Bordawekar, Parsippany, NJ (US)

(72) Inventors: Upkar Bhardwaj, Coram, NY (US); Ann Reese Comfort, New York, NY (US); Ping Li, Basking Ridge, NJ (US); Shoufeng Li, Basking Ridge, NJ (US); Alexey Makarov, Montclair, NJ (US); Mangesh Sadashiv Bordawekar, Parsippany, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/273,874

(22) Filed: May 9, 2014

(65) Prior Publication Data
US 2015/0320749 A1     Nov. 12, 2015

Related U.S. Application Data

(63) Continuation of application No. PCT/US2012/064610, filed on Nov. 12, 2012.

(60) Provisional application No. 61/559,281, filed on Nov. 14, 2011.

(51) Int. Cl.
*A61K 31/506*     (2006.01)
*A61K 9/28*     (2006.01)

(52) U.S. Cl.
CPC ............. *A61K 31/506* (2013.01); *A61K 9/2866* (2013.01); *A61K 9/2893* (2013.01)

(58) Field of Classification Search
None
See application file for complete search history.

(56) References Cited

U.S. PATENT DOCUMENTS

| | | |
|---|---|---|
| 7,943,172 B2 | 5/2011 | Rohrich et al. |
| 2010/0087463 A1 | 4/2010 | Bruneau |
| 2010/0136097 A1 | 6/2010 | Hyde |
| 2011/0165257 A1* | 7/2011 | Rao et al. ............... 424/494 |

FOREIGN PATENT DOCUMENTS

| | | |
|---|---|---|
| WO | 2012/164578 | 12/2012 |
| WO | WO 2012164578 A1 * | 12/2012 |

OTHER PUBLICATIONS

L. Zema et al: "Different HPMC viscosity grades as coating agents for an ora 1 time and/or site-controlled delivery system : An investigation into the mechanisms governing drug release", Journal of Pharmaceutical Sciences, vol. 96, No. 6, Jan. 1, 2007, pp. 1527-1536.

Kleinebudde P: "Roll compaction/dry granulation: pharmaceutical applications". European Journal of Pharmaceutics and Biopharmaceutics, Elsevier Science Publishers B.V., Amsterdam, NL, vo 1 •58, No. 2, Sep. 1, 2004, pp. 317-326.

Parikh D.M., Handbook of Pharmaceutical Granulation Technology, Drugs and the Pharmaceutical Sciences, 2nd ed. Florida: Taylor & Francis Group, 2005, pp. 159-188.

(Continued)

*Primary Examiner* — Carlos Azpuru
*Assistant Examiner* — Casey Hagopian
(74) *Attorney, Agent, or Firm* — Gregory Houghton

(57) ABSTRACT

A solid dosage form of nilotinib is disclosed that comprises: (i) a core comprising 4-Methyl-3-[[4-(3-pyridinyl)-2-pyrimidinyl]amino]-N-[5-(4-methyl-1H-imidazol-1-yl)-3-(trifluoromethyl)phenyl]benzamide or a pharmaceutically acceptable salt thereof and excipients; and (ii) at least one polymer, said polymer coating said core, wherein disintegration of said solid dosage form is delayed.

8 Claims, 6 Drawing Sheets

(56) References Cited

OTHER PUBLICATIONS

Li et al., "The use of hypromellose in oral drug delivery", Journal of Pharmacy and Pharmacology, vol. 57, pp. 533-546, 2005.

Anal, "Time-Controlled-Release Dosage Forms", Pharmaceutical Manufacturing Handbook: Production and Processes, Section 5, Ed. by Shayne Cox Gad, Wiley-Interscience Publication, P. 373, 2008.

* cited by examiner

2101 Pilot PK Data Summary

| | 200 mg | | | |
|---|---|---|---|---|
| | RC1 | RC2 | WG | Ref |
| AUC Inf | 6560 | 9606 | 9669 | 8650 |
| Cmax | 387.8 | 418.7 | 375.9 | 340.3 |
| Cmax ratio | 1.139 | 1.231 | 1.105 | |
| 90% CI | (0.981-1.323) | (1.056-1.435) | (0.951-1.283) | |
| AUC ratio | 0.989 | 1.110 | 1.115 | |
| 90% CI | (0.877-1.116) | (0.982-1.254) | (0.989-1.258) | |

| | 300 mg | | | | 400 mg | | | |
|---|---|---|---|---|---|---|---|---|
| | RC1 | RC2 | WG | Ref | RC1 | RC2 | WG | Ref |
| AUC Inf | 12874 | 12099 | 14377 | 11394 | 11974 | 12565 | 13294 | 11049 |
| Cmax | 514.5 | 472.3 | 493.2 | 396.3 | 482.0 | 543.7 | 467.7 | 373.1 |
| Cmax ratio | 1.298 | 1.192 | 1.244 | | 1.274 | 1.433 | 1.247 | |
| 90% CI | (1.127-1.495) | (1.030-1.378) | (1.081-1.433) | | (1.103-1.471) | (1.243-1.652) | (1.075-1.445) | |
| AUC ratio | 1.130 | 1.051 | 1.262 | | 1.116 | 1.161 | 1.216 | |
| 90% CI | (1.016-1.256) | (0.942-1.172) | (1.135-1.403) | | (0.981-1.270) | (1.020-1.322) | (1.063-1.391) | |

May pass in BE with relaxed criteria [0.7-1.43] & 176 patients

Var A = WG
Var B = RC-1
Var C = RC-2

Figure 6

IMMEDIATE RELEASE 4-METHYL-3-4[[4-(3-PYRIDINYL)-2-PYRIMIDINYL]AMINO]-N-[5-(4-METHYL-1H-IMIDAZOL-1-YL)-3-(TRIFLUOROMETHYL)PHENYL]BENZAMIDE FORMULATION

FIELD OF THE INVENTION

The present invention relates to a pharmaceutical composition comprising a therapeutic compound of nilotinib (Formula I). In particular, the present invention is directed to a pharmaceutical composition that comprises a nilotinib tablet core and that further comprises at least one polymeric coating over the nilotinib core, providing a rapidly disintegrating tablet with a lag time, as compared to an uncoated tablet formulation.

BACKGROUND OF THE INVENTION

Nilotinib is 4-Methyl-3-[[4-(3-pyridinyl)-2-pyrimidinyl]amino]-N-[5-(4-(4-methyl-1H-imidazol-)-3-(trifluoromethyl)phenyl]benzamide. A particularly useful salt of nilotinib is nilotinib hydrochloride monohydrate. These therapeutic compounds have utility as inhibitors of the protein tyrosine kinase (TK) activity of Bcr-Abl. Examples of conditions that may be treated by such therapeutic compounds include, but are not limited to, chronic myeloid leukemia and gastrointestinal stromal tumors.

There is a need to formulate nilotinib and the other therapeutic compounds hereinafter disclosed into pharmaceutical compositions, especially solid oral dosage forms, such that the therapeutic benefits of the compounds may be delivered to a patient in need thereof. One problem to providing such compositions including nilotinib is the physiochemical properties of nilotinib, since nilotinib and its salts are poorly water soluble compounds and are difficult to formulate and deliver (i.e., made bioavailable when ingested orally). It is also difficult to achieve matching pharmacokinetic profiles with different dosage forms, i.e. tablets versus capsules. Another problem is a food effect, as food increases the bioavailability of nilotinib. Compared to a fasted state, nilotinib systemic exposure, as reflected by AUC and $C_{max}$, increases markedly when the unit dosage is given shortly after food is ingested, leading to potential adverse effects in patients.

SUMMARY OF THE INVENTION

The present invention provides a solid dosage form comprising: (i) a core comprising 4-Methyl-3-[[4-(3-pyridinyl)-2-pyrimidinyl]amino]-N-[5-(4-methyl-1H-imidazol-1-yl)-3-(trifluoromethyl)phenyl]benzamide or a pharmaceutically acceptable salt thereof and excipients; and (ii) at least one polymer, said polymer coating said core, wherein disintegration of said solid dosage form is delayed by 4-15 minutes.

The present invention also provides a solid dosage form comprising: (i) a core comprising 4-Methyl-3-[[4-(3-pyridinyl)-2-pyrimidinyl]amino]-N-[5-(4-methyl-1H-imidazol-1-yl)-3-(trifluoromethyl)phenyl]benzamide or a pharmaceutically acceptable salt thereof and excipients; and (ii) at least one polymer, said polymer coating said core, wherein disintegration of said solid dosage form is delayed by 4-15 minutes, said solid dosage form having a fasted state bioavailability equivalent to a hard-gelatin capsule comprising 4-Methyl-3-[[4-(3-pyridinyl)-2-pyrimidinyl]amino]-N-[5-(4-methyl-1H-imidazol-1-yl)-3-(trifluoromethyl)phenyl]benzamide.

The present invention also provides a solid dosage form comprising: (i) a core comprising 4-Methyl-3-[[4-(3-pyridinyl)-2-pyrimidinyl]amino]-N-[5-(4-methyl-1H-imidazol-1-yl)-3-(trifluoromethyl)phenyl]benzamide or a pharmaceutically acceptable salt thereof and excipients; and (ii) at least one polymer, said polymer coating said core, wherein disintegration of said solid dosage form is delayed by 4-15 minutes, said solid dosage form having a reduced $C_{max}$ as compared to an uncoated solid dosage form comprising 4-Methyl-3-[[4-(3-pyridinyl)-2-pyrimidinyl]amino]-N-[5-(4-methyl-1H-imidazol-1-yl)-3-(trifluoromethyl)phenyl]benzamide.

BRIEF DESCRIPTION OF THE DRAWINGS

FIG. 6 summarizes PK data for tablet formulations.

DETAILED DESCRIPTION OF THE INVENTION

Figure 1:
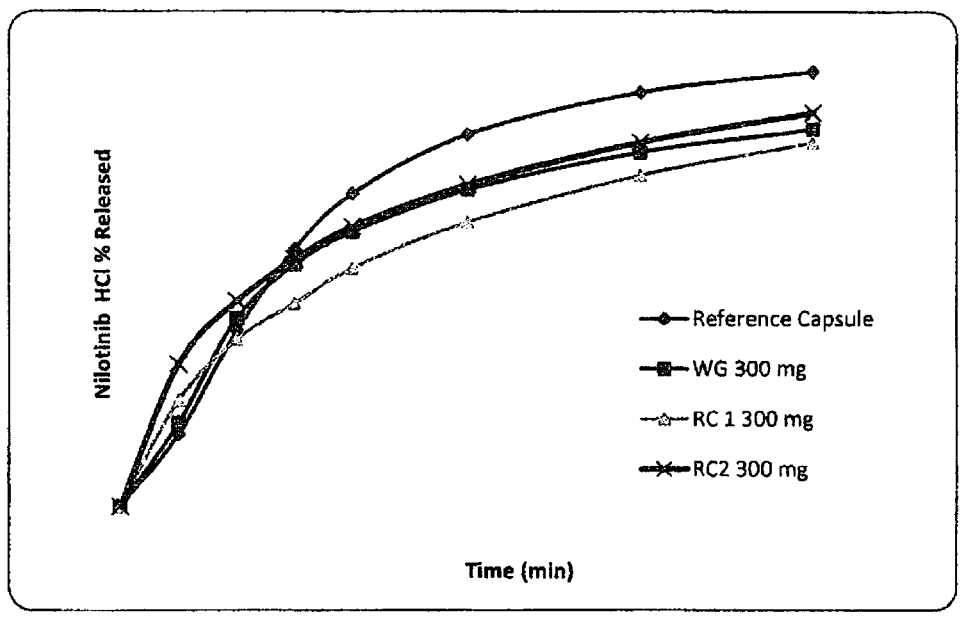
FIG. 1 summarizes dissolution rates for nilotinib tablets (wet granulated and roller compacted) as compared to a nilotinib capsule.
Figure 2:
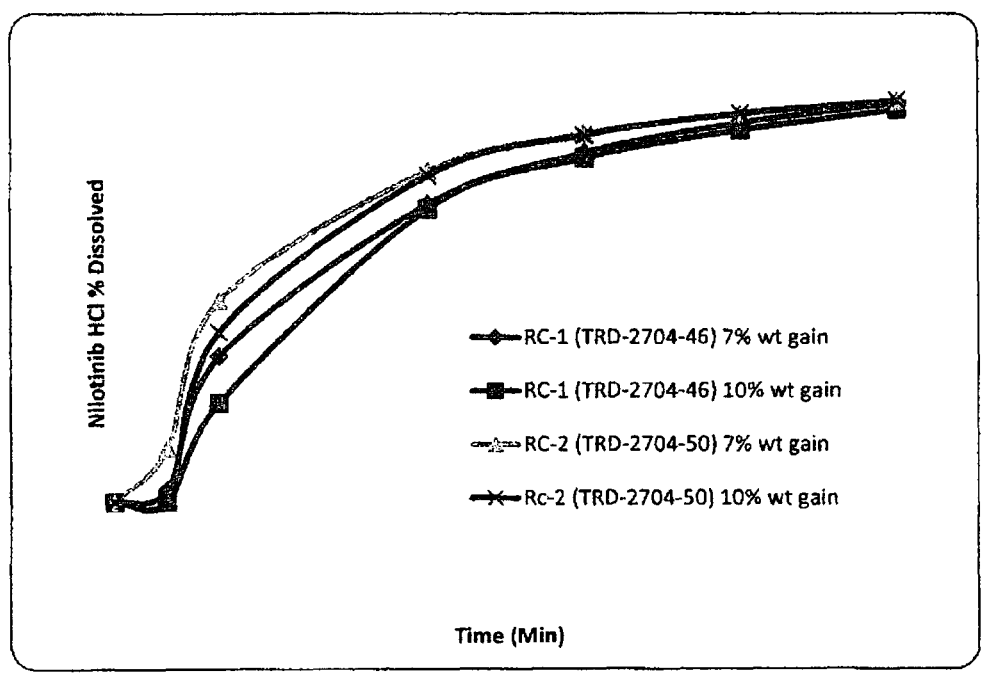
FIG. 2 summarizes dissolution rates for film coated nilotinib tablets (7-10% film coating) at pH 2.0.
Figure 3:
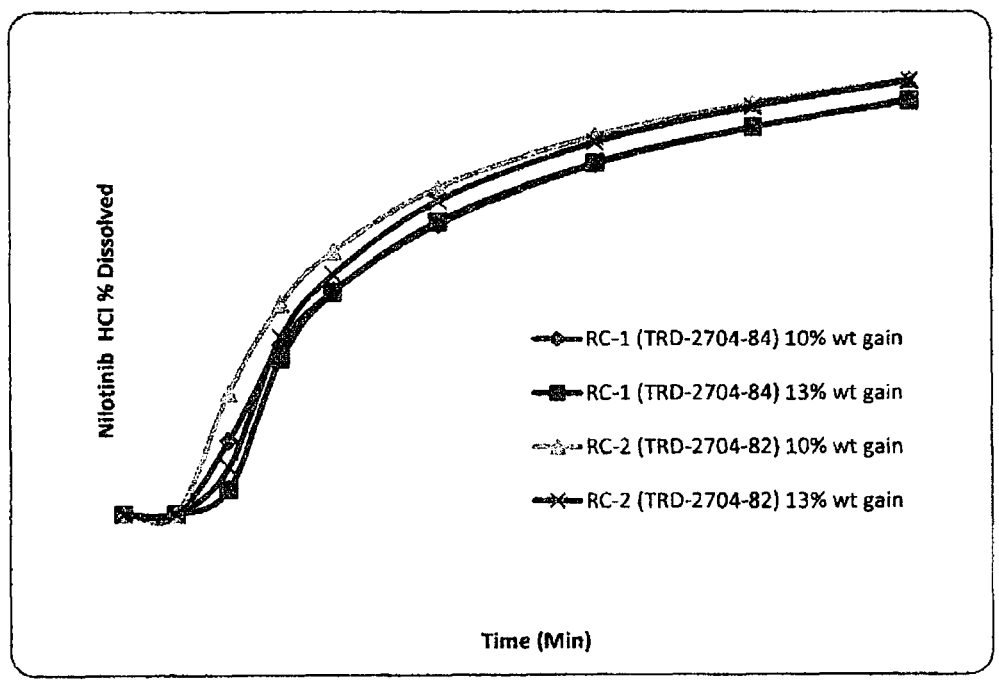
FIG. 3 summarizes dissolution rates for film coated nilotinib tablets (10-13% film coating) at pH 2.0.
Figure 4:
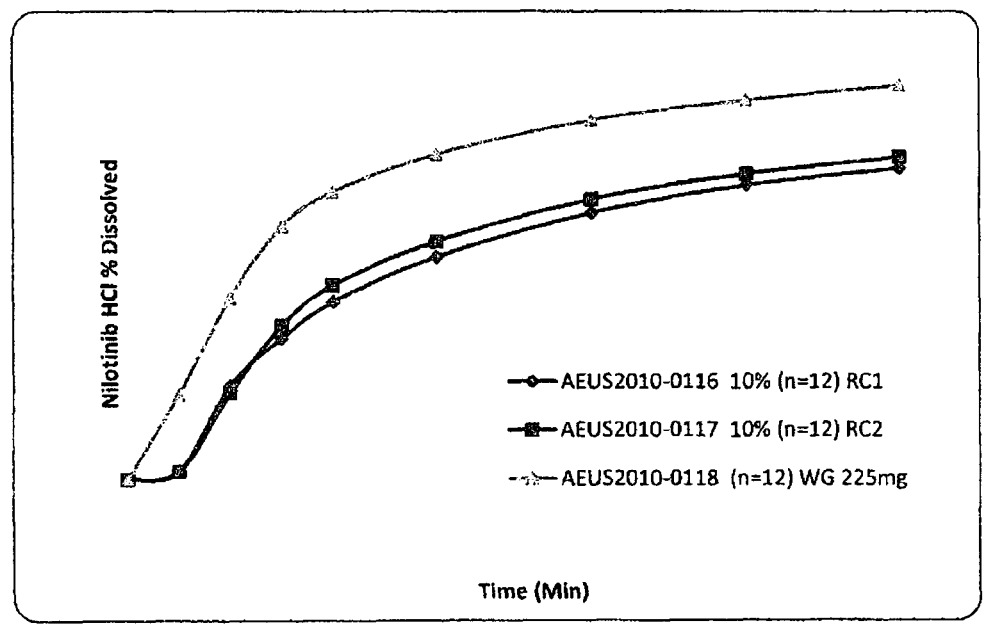
FIG. 4 summarizes dissolution rates for film coated nilotinib tablets prepared by roller compaction (10% film coating) as compared to uncoated nilotinib tablets prepared by wet granulation at pH 2.0.
Figure 5:
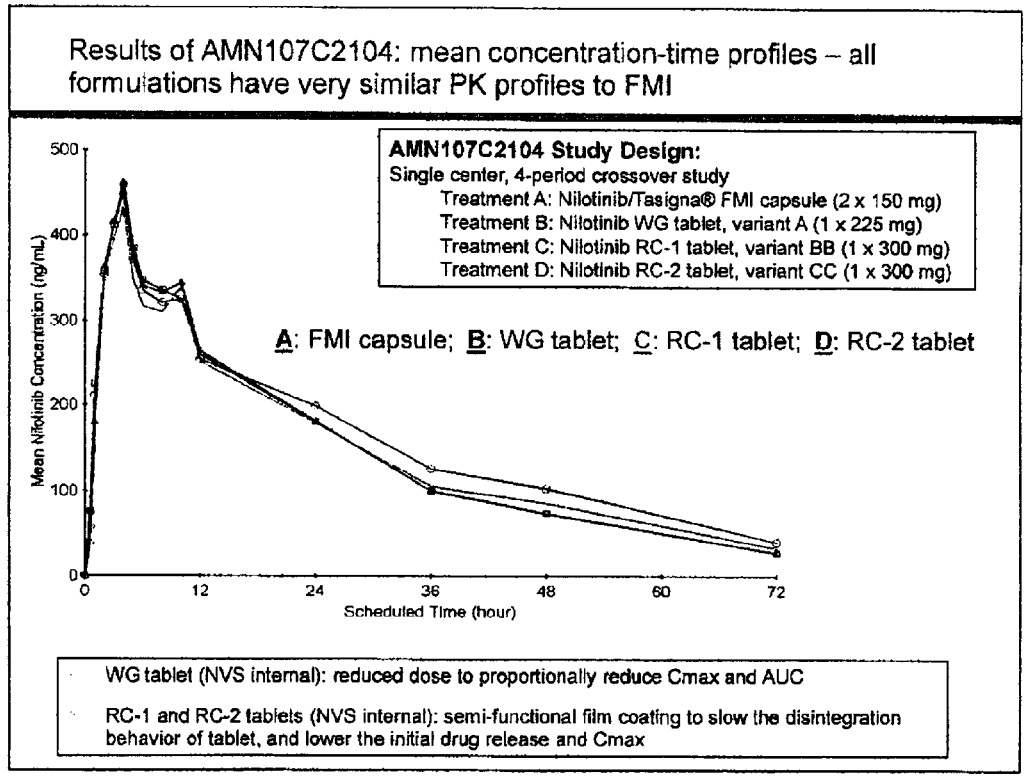
FIG. 5 summarizes a comparison of mean nilotinib concentration versus time profiles for different nilotinib solid dosage forms.

The present invention provides crystalline pharmaceutical compositions of nilotinib or a pharmaceutically acceptable salt thereof formulated in a tablet form to have bioequivalent pharmacokinetic profiles with that of commercially available nilotinib capsule forms As used herein, nilotinib refers to 4-Methyl-3-[[4-(3-pyridinyl)-2-pyrimidinyl]amino]-N-[5-(4-methyl-1H-imidazol-1-yl)-3-(trifluoromethyl)phenyl]benzamide of formula I:

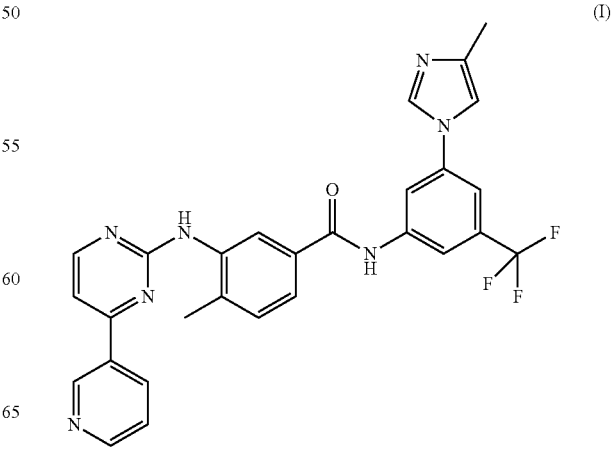

Nilotinib is a member of compounds of formula (II)

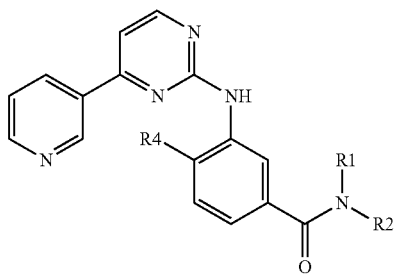

(II)

wherein

R₁ represents hydrogen, lower alkyl, lower alkoxy-lower alkyl, acyloxy-lower alkyl, carboxy-lower alkyl, lower alkoxycarbonyl-lower alkyl, or phenyl-lower alkyl;

R₂ represents hydrogen, lower alkyl, optionally substituted by one or more identical or different radicals R₃, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

and R₃ represents hydroxy, lower alkoxy, acyloxy, carboxy, lower alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

or wherein R₁ and R₂ together represent alkylene with four, five or six carbon atoms optionally mono- or disubstituted by lower alkyl, cycloalkyl, heterocyclyl, phenyl, hydroxy, lower alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, carboxy, phenyl, substituted phenyl, pyridinyl, pyrimidinyl, or pyrazinyl;

R₄ represents hydrogen, lower alkyl, or halogen;

and a N-oxide and to the pharmaceutically acceptable salts of such a compound. Such therapeutic compounds are suitable for the preparation of a pharmaceutical composition for the treatment of kinase dependent diseases, especially Bcr-Abl and Tie-2 kinase dependent diseases, for example, as drugs to treat one or more proliferative diseases.

Within the definition of "therapeutic compound," the prefix "lower" denotes a radical having up to and including a maximum of seven, especially up to and including a maximum of four carbon atoms, the radicals in question being either linear or branched with single or multiple branching.

As used herein, where the plural form is used for compounds, salts, and the like, this is taken to mean also a single compound, salt, or the like.

Any asymmetric carbon atoms may be present in the (R)-, (S)- or (R,S)-configuration, for example in the (R)- or (S)-configuration. The compounds may thus be present as mixtures of isomers or as pure isomers, for example as enantiomer-pure diastereomers. Also contemplated within the present invention is the use of any possible tautomers of the compounds of formula I.

Lower alkyl is for example alkyl with from and including one up to and including seven, for example from and including one to and including four, and is linear or branched; for example, lower alkyl is butyl, such as n-butyl, sec-butyl, isobutyl, tert-butyl, propyl, such as n-propyl or isopropyl, ethyl or methyl. For example lower alkyl is methyl, propyl or tert-butyl.

Lower acyl is for example formyl or lower alkylcarbonyl, in particular acetyl.

An aryl group is an aromatic radical which is bound to the molecule via a bond located at an aromatic ring carbon atom of the radical. In an exemplary embodiment, aryl is an aromatic radical having six to fourteen carbon atoms, especially phenyl, naphthyl, tetrahydronaphthyl, fluorenyl or phenanthrenyl, and is unsubstituted or substituted by one or more, for example up to three, especially one or two substituents, especially selected from amino, mono- or disubstituted amino, halogen, lower alkyl, substituted lower alkyl, lower alkenyl, lower alkynyl, phenyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenylthio, phenyl-lower alkylthio, lower alkylphenylthio, lower alkylsulfinyl, phenylsulfinyl, phenyl-lower alkylsulfinyl, lower alkylphenylsulfinyl, lower alkylsulfonyl, phenylsulfonyl, phenyl-lower alkylsulfonyl, lower alkylphenylsulfonyl, halogen-lower alkylmercapto, halogen-lower alkylsulfonyl, such as especially trifluoromethanesulfonyl, dihydroxybora (—B(OH)2), heterocyclyl, a mono- or bicyclic heteroaryl group and lower alkylene dioxy bound at adjacent C-atoms of the ring, such as methylene dioxy. Aryl is for example phenyl, naphthyl or tetrahydronaphthyl, which in each case is either unsubstituted or independently substituted by one or two substituents selected from the group comprising halogen, especially fluorine, chlorine, or bromine; hydroxy; hydroxy etherified by lower alkyl, e.g. by methyl, by halogen-lower alkyl, e.g. trifluoromethyl, or by phenyl; lower alkylene dioxy bound to two adjacent C-atoms, e.g. methylenedioxy, lower alkyl, e.g. methyl or propyl; halogen-lower alkyl, e.g. trifluoromethyl; hydroxy-lower alkyl, e.g. hydroxymethyl or 2-hydroxy-2-propyl; lower alkoxy-lower alkyl; e.g. methoxymethyl or 2-methoxyethyl; lower alkoxycarbonyl-lower alkyl, e.g. methoxycarbonylmethyl; lower alkynyl, such as 1-propynyl; esterified carboxy, especially lower alkoxycarbonyl, e.g. methoxycarbonyl, n-propoxy carbonyl or iso-propoxy carbonyl; N-mono-substituted carbamoyl, in particular carbamoyl monosubstituted by lower alkyl, e.g. methyl, n-propyl or iso-propyl; amino; lower alkylamino, e.g. methylamino; di-lower alkylamino, e.g. dimethylamino or diethylamino; lower alkylene-amino, e.g. pyrrolidino or piperidino; lower oxaalkylene-amino, e.g. morpholino, lower azaalkylene-amino, e.g. piperazino, acylamino, e.g. acetylamino or benzoylamino; lower alkylsulfonyl, e.g. methylsulfonyl; sulfamoyl; or phenylsulfonyl.

A cycloalkyl group is for example cyclopropyl, cyclopentyl, cyclohexyl or cycloheptyl, and may be unsubstituted or substituted by one or more, especially one or two, substitutents selected from the group defined above as substituents for aryl, e.g., by lower alkyl, such as methyl, lower alkoxy, such as methoxy or ethoxy, or hydroxy, and further by oxo or fused to a benzo ring, such as in benzcyclopentyl or benzcyclohexyl.

Substituted alkyl is alkyl as last defined, especially lower alkyl, for example methyl; where one or more, especially up to three, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially useful.

Mono- or disubstituted amino is especially amino substituted by one or two radicals selected independently of one another from lower alkyl, such as methyl; hydroxy-lower alkyl, such as 2-hydroxyethyl; lower alkoxy lower alkyl, such as methoxy ethyl; phenyl-lower alkyl, such as benzyl or 2-phenylethyl; lower alkanoyl, such as acetyl; benzoyl; substituted benzoyl, wherein the phenyl radical is especially substituted by one or more, for example one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, for example one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and is for example N-lower alkylamino, such as N-methylamino, hydroxy-lower alkylamino, such as 2-hydroxyethylamino or 2-hydroxypropyl, lower alkoxy lower alkyl, such as methoxy ethyl, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl, carbamoyl or aminocarbonylamino. Disubstituted amino is also lower alkylene-amino, e.g. pyrrolidino, 2-oxopyrrolidino or piperidino; lower oxaalkylene-amino, e.g. morpholino, or lower azaalkylene-amino, e.g. piperazino or N-substituted piperazino, such as N-methylpiperazino or N-methoxycarbonylpiperazino.

Halogen is especially fluorine, chlorine, bromine, or iodine, especially fluorine, chlorine, or bromine.

Etherified hydroxy is especially $C_8$-$C_{20}$alkyloxy, such as n-decyloxy, lower alkoxy, such as methoxy, ethoxy, isopropyloxy, or tert-butyloxy, phenyl-lower alkoxy, such as benzyloxy, phenyloxy, halogen-lower alkoxy, such as trifluoromethoxy, 2,2,2-trifluoroethoxy or 1,1,2,2-tetrafluoroethoxy, or lower alkoxy which is substituted by mono- or bicyclic heteroaryl comprising one or two nitrogen atoms, for example lower alkoxy which is substituted by imidazolyl, such as 1H-imidazol-1-yl, pyrrolyl, benzimidazolyl, such as 1-benzimidazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, indolyl or thiazolyl.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, iso-propoxycarbonyl, methoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-Mono- or N,N-disubstituted carbamoyl is especially substituted by one or two substituents independently selected from lower alkyl, phenyl-lower alkyl and hydroxy-lower alkyl, or lower alkylene, oxa-lower alkylene or aza-lower alkylene optionally substituted at the terminal nitrogen atom.

A mono- or bicyclic heteroaryl group comprising zero, one, two or three ring nitrogen atoms and zero or one oxygen atom and zero or one sulfur atom, which groups in each case are unsubstituted or mono- or polysubstituted, refers to a heterocyclic moiety that is unsaturated in the ring binding the heteroaryl radical to the rest of the molecule in formula I and is for example a ring, where in the binding ring, but optionally also in any annealed ring, at least one carbon atom is replaced by a heteroatom selected from the group consisting of nitrogen, oxygen and sulfur; where the binding ring for example has five to twelve, e.g., five or six ring atoms; and which may be unsubstituted or substituted by one or more, especially one or two, substitutents selected from the group defined above as substitutents for aryl, most for example by lower alkyl, such as methyl, lower alkoxy, such as methoxy or ethoxy, or hydroxy. For example the mono- or bicyclic heteroaryl group is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinnolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]pyrazolyl, thienyl and furanyl. For example the mono- or bicyclic heteroaryl group is selected from the group consisting of pyrrolyl, imidazolyl, such as 1H-imidazol-1-yl, benzimidazolyl, such as 1-benzimidazolyl, indazolyl, especially 5-indazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, especially 4- or 8-quinolinyl, indolyl, especially 3-indolyl, thiazolyl, benzo[d]pyrazolyl, thienyl, and furanyl. In one exemplary embodiment of the invention the pyridyl radical is substituted by hydroxy in ortho position to the nitrogen atom and hence exists at least partially in the form of the corresponding tautomer which is pyridin-(1H)2-one. In another exemplary embodiment, the pyrimidinyl radical is substituted by hydroxy both in position 2 and 4 and hence exists in several tautomeric forms, e.g. as pyrimidine-(1H, 3H)2,4-dione.

Heterocyclyl is especially a five, six or seven-membered heterocyclic system with one or two heteroatoms selected from the group comprising nitrogen, oxygen, and sulfur, which may be unsaturated or wholly or partly saturated, and is unsubstituted or substituted especially by lower alkyl, such as methyl, phenyl-lower alkyl, such as benzyl, oxo, or heteroaryl, such as 2-piperazinyl; heterocyclyl is especially 2- or 3-pyrrolidinyl, 2-oxo-5-pyrrolidinyl, piperidinyl, N-benzyl-4-piperidinyl, N-lower alkyl-4-piperidinyl, N-lower alkylpiperazinyl, morpholinyl, e.g. 2- or 3-morpholinyl, 2-oxo-1H-azepin-, 2-tetrahydrofuranyl, or 2-methyl-1,3-dioxolan-2-yl.

Salts are especially the pharmaceutically acceptable salts of compounds of formula I. Such salts are formed, for example, as acid addition salts, for example with organic or inorganic acids, from compounds of formula I with a basic nitrogen atom, especially the pharmaceutically acceptable salts. Suitable inorganic acids include, but are not limited to, halogen acids, such as hydrochloric acid, sulfuric acid, or phosphoric acid.

Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

One useful salt of nilotinib is nilotinib hydrochloride monohydrate, or 4-Methyl-N-[3-(4-methyl-1H-imidazol-1-yl)-5-(trifluromethyl)phenyl]-3-[(4-pyridine-3-ylpyrimidin-2-yl)amino]benzamide hydrochloride hydrate. Suitable salts of nilotinib and polymorphs thereof are disclosed in more general in WO2007/015870 and WO2007/015871.

As used herein the term "pharmaceutical composition" means, for example, a mixture containing a specified amount of a therapeutic compound, e.g. a therapeutically effective amount, of a therapeutic compound in a pharmaceutically acceptable carrier to be administered to a mammal, e.g., a human in order to treat kinase dependent diseases.

As used herein the term "pharmaceutically acceptable" refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

The concentration of therapeutic compound in the pharmaceutical composition is present in an amount, e.g. in a therapeutically effective amount, which will depend on absorption, inactivation and excretion rates of the drug as well as other factors known to one of ordinary skill in the art. Furthermore, it is to be noted that dosage values will also vary with the severity of the condition to be alleviated. It is to be further understood that for any particular recipient, specific dosage regimens should be adjusted over time according to the individual need and the professional judgment of the person administering or supervising the administration of the pharmaceutical compositions. The therapeutic compound may be administered once, or may be divided into a number of smaller doses to be administered at varying intervals of time. Thus, an appropriate amount, e.g. an appropriate therapeutically effective amount, is known to one of ordinary skill in the art.

For example, the dose of the therapeutic compound will be in the range from about 0.1 to about 100 mg per kilogram body weight of the recipient per day. Alternatively lower doses may be given, for example doses of 0.5 to 100 mg; 0.5 to 50 mg; or 0.5 to 20 mg per kilogram body weight per day. The effective dosage range of the pharmaceutically acceptable salts may be calculated based on the weight of the active moiety to be delivered. If the salt exhibits activity itself, the effective dosage may be estimated as above using the weight of the salt, or by other means known to those skilled in the art.

As used herein the term "immediate-release" refers to the rapid release of the majority of the therapeutic compound, e.g., greater than about 50%, about 55%, about 60%, about 65%, about 70%, about 75%, about 80%, or about 90% within a relatively short time, e.g., within 1 hour, 40 minutes, 30 minutes or 20 minutes after oral ingestion. Particularly useful conditions for immediate-release are release of at least or equal to about 80% of the therapeutic compound within thirty minutes after oral ingestion. The particular immediate-release conditions for a specific therapeutic compound will be recognized or known by one of ordinary skill in the art.

As used herein the term "lag time" refers to period of time the majority of the therapeutic compound is delayed from being released after oral ingestion.

As used herein the term "excipient" refers to a pharmaceutically acceptable ingredient that is commonly used in the pharmaceutical technology for preparing granule and/or solid oral dosage formulations. Examples of categories of excipients include, but are not limited to, binders, disintegrants, lubricants, glidants, stabilizers, fillers and diluents. One of ordinary skill in the art may select one or more of the aforementioned excipients with respect to the particular desired properties of the granule and/or solid oral dosage form by routine experimentation and without any undue burden. The amount of each excipient used may vary within ranges conventional in the art. The following references which are all hereby incorporated by reference disclose techniques and excipients used to formulate oral dosage forms. See *The Handbook of Pharmaceutical Excipients*, 4$^{th}$ edition, Rowe et al., Eds., American Pharmaceuticals Association (2003); and *Remington: the Science and Practice of Pharmacy*, 20$^{th}$ edition, Gennaro, Ed., Lippincott Williams & Wilkins (2000).

In an exemplary embodiment of the present invention, the invented solid dosage forms of nilotinib are prepared by roller compacting nilotinib tablet cores and film-coating the nilotinib tablet cores with a functional polymer, wherein disintegration of said solid dosage form is delayed by 4-15 minutes.

The present invention also provides a method of increasing bioavailability by administering the composition or the pharmaceutical composition of the invention, respectively, to an animal or to a patient, wherein the increased bioavailability is determined by comparing the Cmax value or the AUC value of the composition or the pharmaceutical composition of the invention with the composition disclosed in the present invention. Preferably the method increases bioavailability of a drug in administered animal or patient by least 1.3 fold, preferably at least two fold, even more preferably by at least three fold.

In one preferred embodiment of the method, the composition or the pharmaceutical composition of the invention, respectively, comprises 4-methyl-3-[[4-(3-pyridinyl)-2-pyrimidinyl]amino]-N-[5-(4-methyl-1H-imidazol-1-yl)-3-(trifluoromethyl)phenyl]benzamide and has comparable bioavailability when compared with 4-methyl-3-[[4-(3-pyridinyl)-2-pyrimidinyl]amino]-N-[5-(4-methyl-1H-imidazol-1-yl)-3-(trifluoromethyl)phenyl]benzamide in the marketed, commercially available Tasigna™ hard-gelatin capsule manufactured by Novartis. Comparable is defined as 90% CI of $C_{max}$ and AUC within the range of 0.8 and 1.25 when expressed as ratio between the tested (invention formulation) and reference (Tasigna™ capsule formulation) for $C_{max}$ and AUC.

Bioavailability can be measured by skilled artisan by conventional methods. For example, tablets, capsules, liquids, powders, etc., are given orally to humans or animals and blood levels are measured.

The composition or the pharmaceutical composition according to the invention may also comprise one or more binding agents, filling agents, lubricating agents, suspending agents, sweeteners, flavoring agents, preservatives, buffers, wetting agents, effervescent agents and other excipients. Such excipients are known in the art. Examples of filling agents are lactose monohydrate, lactose anhydrous, microcrystalline cellulose, such as Avicel® PH101 and Avicel® PH102, microcrystalline cellulose and silicified microcrystalline cellulose (ProSolv SMCC®), and various starches; examples of binding agents are various celluloses and cross-linked polyvinylpyrrolidone. Suitable lubricants, including agents that act on the flowability of the powder to be compressed, are colloidal silicon dioxide, such as Aerosil® 200, talc, stearic acid, magnesium stearate, calcium stearate and silica gel. Examples of sweeteners are any natural or artificial sweetener, such as sucrose, xylitol, sodium saccharin, cyclamate, aspartame, sucralose, maltitol and acsulfame.

Examples of flavoring agents are Magnasweet® (trademark of MAFCO), bubble gum flavor, and fruit flavors, and the like. Suitable diluents include pharmaceutically acceptable inert fillers, such as microcrystalline cellulose, lactose, dibasic calcium phosphate, saccharides and/or mixtures of any of the foregoing. Examples of diluents include microcrystalline cellulose, such as Avicel® PH101 and Avicel® PH1 02; lactose, such as lactose monohydrate, lactose anhydrous, and Pharmatose® DCL21; dibasic calcium phosphate, such as Emcompress®; mannitol; starch; sorbitol; sucrose; and glucose. Examples of effervescent agents are effervescent couples, such as an organic acid and a carbonate or bicarbonate.

Niliotinib exhibits compressibility problem, coupled with high drug loading >45%, the formulation is also prone to sticking and picking on punches thus requiring high Mg stearate level. The formulation also has friability issues if a suitable binder is not present. To overcome all these challenges, the formulation needs the selected excipients in their optimized amounts.

In one embodiment, the invented core tablets comprise nilotinib in amounts from 30-70% by weight based on the weight of the tablet, Avicel® PH102 (microcrystalline cellulose) as a filler in the range 20-60% by weight, HPC EXF as a binder in the range of 2-6% by weight, crospovidone as a super disintegrant in the range of 2-14% by weight, Aerosil as a glidant or flow enhancer with the range of 0.25 to 4% by weight, Magnesium stearate as an intra-granular (I) component in the range of 0.25-2% by weight and Magnesium stearate as an extra-granular (II) component in the range of 0.7-3.5% by weight based on the weight of the tablet.

In one embodiment, the composition is in an oral solid dosage form. The oral solid dosage form includes tablets, pills, capsules, powders. The oral liquid dosage form includes solutions and suspensions. In one embodiment, the solid dosage form is a polymeric film coated tablet.

Different classes of polymers that may be used to delay the initial release from the tablet are selected from: hydroxypropyl cellulose, hydroxy propyl methyl cellulose, hydroxy propyl ethyl cellulose, ethyl cellulose, shellac, polyvinyl pyrrolidone (e.g K30, K90), polyvinyl acetate, Kollidon VA 64 {Copovidone or (Polyvinyl acetate 40% and polyvinyl pyrrolidone 60%}, Kollidon SR (Polyvinyl acetate 80% and polyvinyl pyrrolidone20%), methacrylic acid (polymers and graft co polymers), carbomer polymers (e.g Carbopol 971P NF, Carbopol 974P NF), veegum, glyceryl behenate/di behenate (Compritol®, hydroxy propyl methyl cellulose acetate succinate (HPMC AS) and hydroxy propyl methyl cellulose phthallate (HPMC-P).

In one aspect, the present invention provides a process of making the composition comprising the steps of blending nilotinib and excipients and roller compacting them to form granules. The granules are compressed into tablets or pills. The nilotinib tablet cores are then film coated to various thicknesses with a polymer coating, providing a lag time before disintegration.

The following examples are given to illustrate the present invention. It should be understood, however, that the invention is not to be limited to the specific conditions or details described in the examples below. The following examples are illustrative, but do not serve to limit the scope of the invention described herein. The examples are meant only to suggest a method of practicing the present invention.

Quantities of ingredients, represented by percentage by weight of the pharmaceutical composition, used in each example are set forth in the respective tables located after the respective descriptions. For a capsule, when calculating the weight of the pharmaceutical composition (i.e. the capsule fill weight), the weight of the capsule shell itself is excluded from the calculation.

Example 1

Nilotinib Tablet Core

One example of a nilotinib tablet core (Formulation A) is summarized in Table 1. The nilotinib tablet cores were prepared by roller compaction. Compared to a commercially available nilotinib capsule formulation developed using a wet granulation technique, the invented nilotinib tablet cores prepared by roller compaction consistently provides nilotinib tablet cores exhibiting excellent compression characteristics, including but not limited to a 6-10 kp compression window, tablet cores having low friability, fast disintegration times (1-2 minutes) and tablet cores that can be compressed at a high speeds.

TABLE 1

Nilotinib Tablet Core (Formulation A)

| Component | % | 200 mg mg/unit | 300 mg mg/unit | 400 mg mg/unit |
|---|---|---|---|---|
| AMN107 (Nilotinib Hydrochloride) | 47.96 | 220.6 | 330.9 | 441.2 |
| Microcrystalline cellulose | 39.04 | 179.6 | 269.4 | 359.2 |
| Hydroxypropylcellulose (HPC EXF) | 3.04 | 14.0 | 21.0 | 28.0 |
| Crospovidone | 6.09 | 28.0 | 42.0 | 56.0 |
| Aerosil 200 PH | 1.00 | 4.6 | 6.9 | 9.2 |
| Magnesium stearate (I) | 0.87 | 4.0 | 6.0 | 8.0 |
| Magnesium stearate (II) | 2.00 | 9.2 | 13.8 | 18.4 |
| Core tablet weight | 100.00 | 460.0 | 690.0 | 920.0 |

Unit dosages of 50 mg and 100 mg were also manufactured from nilotinib tablet core formulation A. The unit dosages were prepared in proportion to the 200 mg, 300 mg and 400 mg unit doses.

Example 2

Nilotinib Tablet Core

Another example of a nilotinib tablet core (Formulation B) is summarized in Table 2. The nilotinib tablet cores were prepared by roller compaction. Compared to a commercially available nilotinib capsule formulation developed using a wet granulation technique, the invented nilotinib tablet cores prepared by roller compaction consistently provides nilotinib tablet cores exhibiting excellent compression characteristics, including but not limited to a 6-10 kp compression window, tablet cores having low friability, fast disintegration times (1-2 minutes) and tablet cores that can be compressed at a high speeds.

TABLE 2

Nilotinib Tablet Core (Formulation B)

| Component | % | 200 mg mg/unit | 300 mg mg/unit | 400 mg mg/unit |
|---|---|---|---|---|
| AMN107 (Nilotinib Hydrochloride) | 47.96 | 220.6 | 330.9 | 441.2 |
| Microcrystalline cellulose | 35.13 | 161.6 | 242.4 | 323.2 |
| Hydroxypropylcellulose | 3.04 | 14.0 | 21.0 | 28.0 |
| Crospovidone | 10.00 | 46.0 | 69.0 | 92.0 |

TABLE 2-continued

Nilotinib Tablet Core (Formulation B)

| Component | % | 200 mg mg/unit | 300 mg mg/unit | 400 mg mg/unit |
|---|---|---|---|---|
| Aerosil 200 PH | 1.00 | 4.6 | 6.9 | 9.2 |
| Magnesium stearate (I) | 0.87 | 4.0 | 6.0 | 8.0 |
| Magnesium stearate (II) | 2.00 | 9.2 | 13.8 | 18.4 |
| Core tablet weight | 100.00 | 460.0 | 690.0 | 920.0 |

Unit dosages of 50 mg and 100 mg were also manufactured from nilotinib tablet core formulation A. The unit dosages were prepared in proportion to the 200 mg, 300 mg and 400 mg unit doses.

Manufacturing Process

Nilotinib was mixed with Aerosil 200 PH, HPC EXF, and Crospovidone. Microcrystalline cellulose was added and the mixture was blended. The blended mixture was then sieved through a #16 to #35 screen. Magnesium stearate (I) was added to the sieved mixture and was again blended to distribute Magnesium stearate. This mixture was roller compacted using a compaction force of 15-40 kN on a 50 mm roller compactor. The ribbons were then milled through a sieve (range 10-18 US mesh size). Milled granules were blended with magnesium stearate (II) to distribute magnesium stearate.

Dissolution

Two step dissolution conditions were used for the following nilotinib table cores (formulation A and B), wet granulated nilotinib formulation capsule, and nilotinib capsule formulation: 37° C.; Step 1, 0-60 minutes 500 ml pH 2 buffer, Step 2, >60 minutes 1000 ml pH 6.8 buffer; Paddle at 75 rpm.

The invented nilotinib tablet cores prepared from roller compacted nilotinib formulations A and B exhibit fast disintegration times (<2 min), irrespective of the compression force and hardness of the tablet, as compared to the commercially available nilotinib capsule formulation (FIG. 1). For the invented nilotinib tablet cores to be bio-equivalent with the commercial nilotinib capsule formulation, a dissolution lag time was required to delay the disintegration time of the nilotinib tablet cores. This lag time (4-12 minutes) is achieved using a functional polymer based coating over core tablets, preventing the tablets from disintegrating before the lag time.

Film Coated Nilotinib Tablet Cores

The composition of film coated nilotinib tablets is summarized in Table 3. Film coated nilotinib tablet cores were prepared from nilotinib formulations A and B.

TABLE 3

Composition of film coated nilotinib tablets (Formulations A and B)

| Composition | RC Formulation A % | RC Formulation A (mg) | RC Formulation B % | RC Formulation B (mg) |
|---|---|---|---|---|
| AMN107 HCl | 43.60 | 330.90 | 43.57 | 330.90 |
| Avicel PH102 | 35.61 | 270.30 | 31.95 | 242.70 |
| HPC EXF | 2.73 | 20.70 | 2.73 | 20.70 |
| Crospovidone | 5.45 | 41.40 | 9.08 | 69.00 |
| Aerosil 200 | 0.91 | 6.90 | 0.91 | 6.90 |
| Mg stearate | 2.61 | 19.80 | 2.61 | 19.80 |
| PEG 4000 | | | 0.48 | 3.68 |
| HPMC E50 | 1.52 | 11.50 | 3.23 | 24.50 |
| Opadry White | 7.32 | 55.57 | 5.20 | 39.46 |
| Opadry Yellow | 0.24 | 1.84 | 0.17 | 1.31 |
| Opadry Red | 0.01 | 0.09 | 0.08 | 0.60 |
| Total | 100.00 | 759.00 | 100.00 | 759.55 |

Film coating thickness can be varied based upon weight gain of nilotinib tablet cores. An increased disintegration time is observed with corresponding increase in the weight gain of film coating.

The opadry white, yellow and red impart a pale yellow color to the tablets and are only present for aesthetic value, whereas HPMC E50 is the functional polymer that delays the disintegration time.

The functional coating provides a unique dissolution profile with the following characterstics:

1) For 7% functional coating weight gain the following dissolution profile in 900 ml pH 2.0 is observed
   0-8% dissolved at 5 minutes
   20-30% dissolved at 10 minutes
   35-45% dissolved at 15 minutes
   45-60% dissolved in 30 minutes 2) For 10% functional coating weight gain the following dissolution profile in 900 ml pH 2.0 is observed
   0-5% dissolved at 5 minutes
   10-25% dissolved at 10 minutes
   25-45% dissolved at 15 minutes
   45-55% dissolved in 30 minutes 3) For 13% functional coating weight gain the following dissolution profile in 900 ml pH 2.0 is observed
   0% dissolved at 5 minutes
   2-10% dissolved at 10 minutes
   20-35% dissolved at 15 minutes
   45-55% dissolved in 30 minutes

TABLE 4

Dissolution profiles of different weight % functional coating weight gain at pH 2.0

| Batches | Average % released at time (min) | | | | | | | | Paddle (rpm) |
|---|---|---|---|---|---|---|---|---|---|
| | 0 | 5 | 10 | 15 | 20 | 30 | 45 | 60 | |
| TRD-2704-084__10% RC1 | 0 | 0 | 13 | 29 | 38 | 49 | 60 | 66 | 50 |
| TRD-2704-084__13% RC1 | 0 | 0 | 4 | 27 | 38 | 50 | 60 | 66 | 50 |
| TRD-2704-082__10% RC2 | 0 | 0 | 21 | 36 | 45 | 56 | 65 | 70 | 50 |
| TRD-2704-082__13% RC2 | 0 | 0 | 8 | 30 | 41 | 54 | 64 | 70 | 50 |
| AEUS2010-0116 10% (n = 12) RC1 | 0 | 2 | 21 | 32 | 41 | 51 | 61 | 67 | 50 |
| AEUS2010-0117 10% (n = 12) RC2 | 0 | 2 | 20 | 35 | 45 | 55 | 64 | 70 | 50 |
| TRD-2704-040__7% RC1 | 0 | 2 | 24 | 36 | 43 | 53 | 62 | 68 | 50 |
| TRD-2704-042__7% RC2 | 0 | 2 | 27 | 40 | 46 | 56 | 64 | 70 | 50 |

Human PK Results

In the first study the tablet formulation without any functional coating were tested in humans. The results are as given in FIG. 6.

It can be seen from FIG. 6 that none of the formulations was bioequivalent to the reference marketed capsule formulation, whereas the all dosage forms exhibited a higher $C_{max}$ as compared with the reference marketed capsule formulation, whereas the ratio of $C_{max}$ is disproportionally higher than the ratio of AUC.

In another study, 300 mg RC variants with 10% film coating were tested for BE and the results are as shown below.

PK results of the variants BB (RC1 with 10% film coating) and Variant CC (RC2 with 10% film coating).

Results of AMN107C2104: summary of PK parameters – geometric mean ratio for all formulations within BE range (80-125%)

| Parameter | A (N = 19) | B (N = 19) | C (N = 18) | D (N = 18) | Geometric Mean Ratio (90% CIs) | | |
|---|---|---|---|---|---|---|---|
| | | | | | B vs. A | C vs. A | D vs. A |
| $C_{max}$ (ng/mL) | 449.27 (29.8) | 479.97 (25.4) | 453.18 (33.6) | 478.66 (37.4) | 1.07 (0.92, 1.24) | 1.01 (0.87, 1.17) | 1.07 (0.92, 1.23) |
| $AUC_{0\text{-}tlast}$ (ng·h/mL) | 10948.36 (32.2) | 10193.73 (27.2) | 10026.16 (33.5) | 9898.25 (37.3) | 0.93 (0.82, 1.05) | 0.92 (0.81, 1.04) | 0.90 (0.80, 1.02) |
| $AUC_{0\text{-}inf}$ (ng·h/mL) | 12151.57 (38.6) | 10632.62 (29.1) | 11303.04 (36.8) | 10784.07 (42.7) | 0.88 (0.76, 1.00) | 0.93 (0.81, 1.06) | 0.89 (0.78, 1.02) |
| $t_{max}$ (h) | 4.00 (2.05, 10.00) | 4.00 (2.00, 10.02) | 4.00 (2.00, 10.00) | 4.00 (2.00; 10.00) | 0.00 (-2.00, 5.99) | 0.00 (-3.00, 1.98) | 0.00 (-2.00, 1.97) |

A: FMI capsule; B: WG tablet; C: RC-1 tablet; D: RC-2 tablet

Bioequivalence was demonstrated for RC1 and RC2 variants with functional film coating for 300 mg strength.

What is claimed:

1. A solid dosage form comprising: (i) a core comprising 4-Methyl-3-[[4-(3-pyridinyl)-2-pyrimidinyl]amino]-N-[5-(4-methyl-1H-imidazol-1-yl)-3-(trifluoromethyl)phenyl]benzamide or a pharmaceutically acceptable salt thereof and excipients; and (ii) at least one polymer, said polymer coating said core, wherein disintegration of said solid dosage form is delayed 4-15 minutes, and wherein 7-13% of the solid dosage form is the polymer that coats the core.

2. The solid dosage form of claim 1, wherein the polymer is hydroxypropylmethyl cellulose.

3. The solid dosage form of claim 1, wherein 0-8% of the solid dosage form is dissolved after 5 minutes at pH 2.0.

4. The solid dosage form of claim 1, wherein 45-60% of the solid dosage form is dissolved after 30 minutes at pH 2.0.

5. A solid dosage form comprising: (i) a core comprising 4-Methyl-3-[[4-(3-pyridinyl)-2-pyrimidinyl]amino]-N-[5-(4-methyl-1H-imidazol-1-yl)-3-(trifluoromethyl)phenyl]benzamide or a pharmaceutically acceptable salt thereof and excipients; and (ii) at least one polymer, said polymer coating said core and wherein 7-13% of the solid dosage form is the polymer that coats the core, having a fasted state bioavailability equivalent to a hard gelatin capsule, wherein its $C_{max}$ and AUC are in the bioequivalent range when compared with capsules comprising 4-Methyl-3-[[4-(3-pyridinyl)-2-pyrimidinyl]amino]-N-[5-(4-methyl-1H-imidazol-1-yl)-3-(trifluoromethyl)phenyl]benzamide or a pharmaceutically acceptable salt thereof.

6. The solid dosage form of claim 5, wherein the polymer is hydroxypropylmethyl cellulose.

7. The solid dosage form of claim 5, wherein 0-8% by weight of the solid dosage form is dissolved after 5 minutes at pH 2.0.

8. The solid dosage form of claim 5, wherein 45-60% by weight of the solid dosage form is dissolved after 30 minutes at pH 2.0.

* * * * *